United States Patent
Terry

(10) Patent No.: US 12,390,930 B2
(45) Date of Patent: Aug. 19, 2025

(54) ROBOTIC IMAGING SYSTEM WITH FORCE-BASED COLLISION AVOIDANCE MODE

(71) Applicant: Alcon Inc., Fribourg (CH)

(72) Inventor: Patrick Terry, Goleta, CA (US)

(73) Assignee: Alcon Inc., Fribourg (CH)

(*) Notice: Subject to any disclaimer, the term of this patent is extended or adjusted under 35 U.S.C. 154(b) by 259 days.

(21) Appl. No.: 18/112,597

(22) Filed: Feb. 22, 2023

(65) Prior Publication Data

US 2023/0278217 A1 Sep. 7, 2023

Related U.S. Application Data

(60) Provisional application No. 63/315,129, filed on Mar. 1, 2022.

(51) Int. Cl.
| | |
|---|---|
| *B25J 19/02* | (2006.01) |
| *B25J 9/04* | (2006.01) |
| *B25J 9/16* | (2006.01) |
| *B25J 13/08* | (2006.01) |
| *B25J 15/00* | (2006.01) |
| *B25J 5/00* | (2006.01) |

(52) U.S. Cl.
CPC ............ *B25J 9/1666* (2013.01); *B25J 9/045* (2013.01); *B25J 9/1607* (2013.01); *B25J 9/1633* (2013.01);
(Continued)

(58) Field of Classification Search
CPC . A61B 90/361; A61B 90/50; A61B 2090/064; B25J 19/023; B25J 9/1633;
(Continued)

(56) References Cited

U.S. PATENT DOCUMENTS

| | | | | |
|---|---|---|---|---|
| 8,781,630 B2* | 7/2014 | Banks | ...................... | A61B 6/12 378/197 |
| 8,792,964 B2* | 7/2014 | Maschke | ................ | A61B 6/503 600/427 |

(Continued)

FOREIGN PATENT DOCUMENTS

| | | |
|---|---|---|
| WO | 2014139023 A1 | 9/2014 |
| WO | 2017040821 A1 | 3/2017 |

OTHER PUBLICATIONS

Zielinski et al., Applications of MRROC++ Robot Programming Framework, 2005, IEEE, p. 251-257 (Year: 2005).*

(Continued)

*Primary Examiner* — McDieunel Marc
(74) *Attorney, Agent, or Firm* — Nayyer J. Siddiqi; Quinn IP Law

(57) ABSTRACT

A robotic imaging system includes a camera configured to obtain one or more images of a target site. A robotic arm is operatively connected to the camera, the robotic arm being adapted to selectively move the camera in a movement sequence. A force-based sensor is configured to detect and transmit sensor data related to at least one of force and/or torque imparted by a user for moving the camera. The system includes a controller configured to receive the sensor data. The controller has a processor and tangible, non-transitory memory on which instructions are recorded. The controller is adapted to selectively execute a collision avoidance mode, including applying a respective correction force to modify the movement sequence when the camera and/or the robotic arm enter a predefined buffer zone.

20 Claims, 5 Drawing Sheets

(52) U.S. Cl.
CPC ......... *B25J 13/084* (2013.01); *B25J 15/0019*
(2013.01); *B25J 19/023* (2013.01); *B25J 5/007*
(2013.01)

(58) Field of Classification Search
CPC ...... B25J 9/1607; B25J 13/084; B25J 9/1666;
B25J 9/045; B25J 15/0019; B25J 5/007;
G05B 2219/40477
See application file for complete search history.

(56) References Cited

U.S. PATENT DOCUMENTS

| | | | |
|---|---|---|---|
| 2019/0327394 A1* | 10/2019 | Ramirez Luna | H04N 23/51 |
| 2023/0086411 A1* | 3/2023 | Terry | A61B 34/74 |
| | | | 700/245 |
| 2023/0278218 A1* | 9/2023 | Terry | B25J 9/1676 |
| | | | 700/255 |

OTHER PUBLICATIONS

Zhang et al., A two-arm situated artificial communicator for human-robot cooperative assembly, 2003, IEEE, p. 651-658 (Year: 2003).*
Iossifidis et al., Anthropomorphism as a pervasive design concept for a robotic assistant, 2003, IEEE, p. 3465-3472 (Year: 2003).*
Asfour et al., ARMAR-6: A High-Performance Humanoid for Human-Robot Collaboration in Real-World Scenarios, 2019, IEEE, p. 106-121 (Year: 2019).*

* cited by examiner

ROBOTIC IMAGING SYSTEM WITH FORCE-BASED COLLISION AVOIDANCE MODE

CROSS-REFERENCE TO RELATED APPLICATION

The present application claims the benefit of priority to U.S. Provisional Application No. 63/315,129 filed Mar. 1, 2022, which is hereby incorporated by reference in its entirety.

INTRODUCTION

The present disclosure relates generally to a robotic imaging system. More specifically, the disclosure relates to a collision avoidance mode in a robotic imaging system. Various imaging modalities are commonly employed to image different parts of the human body. Robotic systems have been developed to improve the efficiency of medical procedures employing these imaging modalities. The robotic systems may incorporate multiple parts or components to assist users in operating the system. As such, it may be challenging to avoid self-collisions of the multiple components, for example, one robot link with another, collisions of the camera unit with the robotic arm and/or storage unit, and collisions of the camera unit with the image plane.

SUMMARY

Disclosed herein is a robotic imaging system having a camera configured to obtain one or more images of a target site. A robotic arm is operatively connected to the camera, the robotic arm being adapted to selectively move the camera in a movement sequence. A force-based sensor is configured to detect and transmit sensor data related to at least one of force and/or torque imparted by a user for moving the camera. The system includes a controller configured to receive the sensor data. The controller has a processor and tangible, non-transitory memory on which instructions are recorded. The controller is adapted to selectively execute a collision avoidance mode, including applying a respective correction force to modify the movement sequence when at least one of the camera and the robotic arm enter a predefined buffer zone.

The camera may be a stereoscopic camera configured to record left and right images for producing at least one stereoscopic image of the target site. The force-based sensor may include a six-degrees-of-freedom haptic force-sensing device. The controller is adapted to calculate the respective correction force using a closed-loop control module, including at least one of a proportional-integral controller, a proportional-derivative controller and a proportional-integral-derivative controller. In some embodiments, the predefined buffer zone is within a delta value of at least one keep-out zone, with application of the respective correction force pushing at least one of the camera and the robotic arm away from the at least one keep-out zone.

The controller may be adapted to calculate the respective correction force for one or more checkpoints each having a respective position and respective speed along a first direction. The robotic imaging system may include a head unit for housing the camera and a coupling plate mechanically coupling the head unit to the robotic arm, the head unit being operatively connected to a cart. The checkpoints may be located on at least one of the head unit, the coupling plate and the robotic arm. The controller may be adapted to calculate the respective correction force using a proportional-derivative controller as: $F=[K_p(b-x)+K_d(0-\dot{x})]$, with F denoting the respective correction force, b denoting a respective buffering distance to the at least one keep-out zone, x and $\dot{x}$ denoting the respective position and respective speed of the one or more checkpoints, and $K_p$ and $K_d$ denoting respective tunable gain factors of the proportional-derivative controller.

The controller may be adapted to execute a joint limit calculation, with the respective correction force including a force contribution from the joint limit calculation. Executing the joint limit calculation may include determining a respective torque for the at least one joint, via a closed-loop module and converting the respective torque to a respective tool force using a transpose of a Jacobian matrix. The force contribution is based on a sum of the respective tool force for each of the one or more joints.

The robotic imaging system may include a cart operatively connected to the robotic arm. The respective correction force may include a force contribution from a cart limit calculation. The controller is adapted to execute the cart limit calculation, including calculating a respective spherical distance and a respective speed of one or more checkpoints from a surface of the cart. The controller is adapted to obtain a radial force when the respective spherical distance is below a predefined threshold. The force contribution may be obtained as the radial force multiplied by a fraction. The surface of the cart may be modelled as a sphere and the respective spherical distance (r) may be obtained as: $r=\sqrt{(w_0-s_0)^2+(w_1-s_1)^2+(w_2-s_2)^2}$, with ($w_0$, $w_1$, $w_2$) denoting respective coordinates of the one or more checkpoints and ($s_0$, $s_1$, $s_2$) denoting the respective coordinates of a center of the sphere. The respective speed ($\dot{r}$) may be obtained based in part on the respective coordinates of the center of the sphere and a time derivative of the respective coordinates of the one or more checkpoints. The respective speed ($\dot{r}$) may be obtained as $$\dot{r} = \frac{\dot{w}_0(w_0 - s_0) + \dot{w}_1(w_1 - s_1) + \dot{w}_2(w_2 - s_2)}{r},$$

with ($\dot{w}_0$, $\dot{w}_1$, $\dot{w}_2$) denoting the time derivative of the respective coordinates of the one or more checkpoints. The controller may be adapted to calculate the radial force based in part on a respective buffering distance to at least one keep-out zone, the respective spherical distance and the respective speed. The radial force may be obtained as: $[F_R=[K_p(b-r)+K_d(0-\dot{r})]$, where r is the respective spherical distance, $\dot{r}$ is the respective speed, b is the respective buffering distance to the at least one keep-out zone, and $K_p$, $K_d$ are a plurality of tunable constants of a proportional-derivative controller.

In some embodiments, the respective correction force may include a force contribution from a boundary plane limit calculation. The controller is adapted to execute the boundary plane limit calculation, including obtaining at least one boundary plane perpendicular relative to a first direction and calculating a respective distance and a respective speed of one or more checkpoints from the at least one boundary plane along the first direction. The controller is adapted to obtain respective force components when the respective distance is below a predefined threshold. The force contribution is obtained as a sum of each of the respective force components. The boundary plane may be in proximity to a patient.

The controller may be adapted to calculate the respective force components based in part on a respective buffering distance to at least one keep-out zone, the respective distance and the respective speed from the at least one boundary plane. The respective force components ($F_i$) may be obtained as: $[F_i=[K_p(b-z)+K_d(0-\dot{z})]$, where z is the respective distance from the at least one boundary plane, $\dot{z}$ is the respective speed, b is the respective buffering distance to the at least one keep-out zone, and $K_p$, $K_d$ are a plurality of tunable constants of a proportional-derivative controller.

The above features and advantages and other features and advantages of the present disclosure are readily apparent from the following detailed description of the best modes for carrying out the disclosure when taken in connection with the accompanying drawings.

Figure 1:
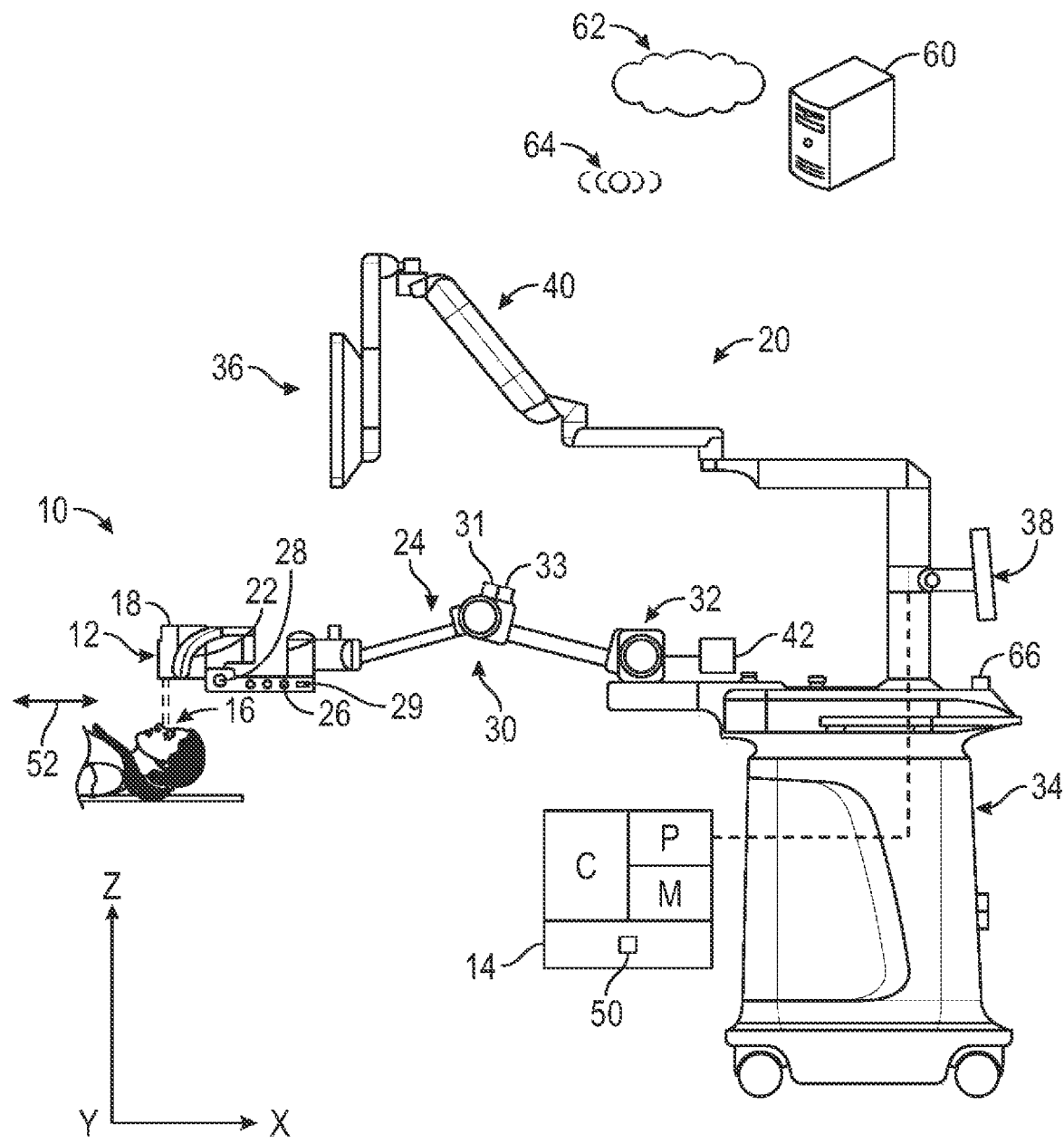
FIG. 1 is a schematic fragmentary diagram of a robotic imaging system having a camera, and a controller with a collision avoidance mode.

Representative embodiments of this disclosure are shown by way of non-limiting example in the drawings and are described in additional detail below. It should be understood, however, that the novel aspects of this disclosure are not limited to the particular forms illustrated in the above-enumerated drawings. Rather, the disclosure is to cover modifications, equivalents, combinations, sub-combinations, permutations, groupings, and alternatives falling within the scope of this disclosure as encompassed, for instance, by the appended claims.

DETAILED DESCRIPTION

Referring to the drawings, wherein like reference numbers refer to like components, FIG. 1 schematically illustrates a robotic imaging system 10 having a camera 12 with a collision avoidance mode 14. The robotic imaging system 10 is configured to image a target site 16. While the camera 12 shown in FIG. 1 is a stereoscopic camera 12, it is understood that other types of cameras may be employed (e.g., those taking a single image). Referring to FIG. 1, the camera 12 is at least partially located in a head unit 18 of a housing assembly 20, with the head unit 18 configured to be at least partially directed towards the target site 16. The camera 12 is configured to record first and second images of the target site 16, which may be employed to generate a live two-dimensional stereoscopic view of the target site 16. The target site 16 may be an anatomical location on a patient, a laboratory biological sample, calibration slides/templates, etc.

Referring to FIG. 1, the robotic imaging system 10 includes a controller C having at least one processor P and at least one memory M (or non-transitory, tangible computer readable storage medium) on which instructions are recorded for executing method 100, described below with respect to FIG. 2, of operating the collision avoidance mode 14. The memory M can store controller-executable instruction sets, and the processor P can execute the controller-executable instruction sets stored in the memory M.

Referring to FIG. 1, at least one input device 22 ("at least one" omitted henceforth) is operatively connected to the camera 12 (e.g., at the head unit 18) to allow a user to manually position the camera 12. The input device 22 may include respective controls for activating or selecting specific features of the camera 12, such as focus, magnification, adjusting an amount/type of light projected onto the target site 16 and other features. It is understood that the number and form of the input devices 22 may be varied, for example, the input device 22 may include a joystick, wheel, mouse or touchscreen device. In some embodiments, the input device 22 may be controlled via a remote control 66 (see FIG. 1).

Referring to FIG. 1, the robotic imaging system 10 includes a robotic arm 24 operatively connected to and configured to selectively move the head unit 18. The head unit 18 may be mechanically coupled to the robotic arm 24 via a coupling plate 26. The user may position and orient the camera 12 with assistance from the robotic arm 24. Referring to FIG. 1, a force-based sensor 28 is operatively connected to the robotic arm 24 and/or coupling plate 26. The force-based sensor 28 is configured to detect forces and/or torque imparted by a user for moving the camera 12. The force-based sensor 28 is adapted to detect a user's movement or force on the camera 12 and convert the detected force/movement into rotational and/or translational data.

The robotic arm 24 includes one or more joints, such as first joint 30 and second joint 32, configured to provide further degrees of positioning and/or orientation of the head unit 18. The data from the force-based sensor 28 may be employed to determine which joints of the robotic arm 24 are to be rotated and how quickly the joints should be rotated, in order to provide assisted movement of the camera 12. Referring to FIG. 1, a respective joint motor (such as joint motor 31) and a respective joint sensor (such as joint sensor 33), may be coupled to each joint. The joint motor 31 is configured to rotate the first joint 30 around an axis, while the joint sensor 33 is configured to transmit the position (in 3D space) of the first joint 30.

The collision avoidance mode 14 is force-based and acts on acceleration dynamics to avoid self-collisions of the various components, for example, collisions of the camera 12 with the robotic arm 24, collisions of the camera 12 with a storage unit (e.g., cart 34) and collisions of the first joint 30 with the second joint 32. The collision avoidance mode 14 described herein provides smooth transitions and is a part of the dynamics of the control system.

The robotic arm 24 includes an assisted drive function 50 incorporating a user-guided control system. In one embodiment, a user may hold the input device 22 and actuate or push a release button. Actuation of the release button causes the camera 12 to transmit a message to the controller C indicative that a user desires to begin the assisted drive function 50. The controller C configures the robotic arm 24 and/or the coupling plate 26 to enable the user to gently steer the camera 12 in a desired direction. During this movement, the controller C causes the robotic arm 24 and/or the coupling plate 26 to move the camera 12 in a "power steering" manner, safely supporting its weight and automatically determining which joints should be activated and which should be braked in a coordinated manner to achieve the user's desired movement.

In some embodiments, the robotic arm 24 may permit user movement without assistance, or at least initial assistance. In these examples, the force-based sensor 28 detects motion imparted by the user, which is used by the robotic imaging system 10 to subsequently cause one or more joints to rotate, thereby providing assisted movement. The time between initial detection of motion or the force resulting in the motion, until the robotic imaging system 10 causes the joints to rotate for a short time, e.g., less than 200 milliseconds, or as few as 10 milliseconds, where the user does not notice the initial time of unassisted movement of the robotic arm 24.

The force-based sensor 28 may include a six-degrees-of-freedom haptic force-sensing module. In these embodiments, the force-based sensor 28 may detect translational force or motion in the X-axis, Y-axis, and Z-axis and separately detect rotational force or motion around a yaw-axis, a pitch-axis, and a roll-axis. The decoupling of the translational force and the rotational force may enable the robotic imaging system 10 to calculate direct and/or reverse kinematics for control of the robotic arm 24. The force-based sensor 28 may include an opto-sensor (e.g., force/torque sensor) that enables the robotic arm 24 to respond electromechanically to a user's gentle push on the camera 12. The opto-sensor may include an electro-optical device configured to transform applied forces and/or torques into electrical signals, thereby enabling a desired force/torque input by a user to be sensed and transformed into a motion request that is provided in the sensed linear and/or rotational direction(s). It is understood that other types of sensor technologies may be employed. For example, the force-based sensor 28 may include a strain gauge or piezoelectric device that is configured to sense a haptic signal from a user.

The position of the force-based sensor 28 may be varied based on the application at hand, for example, at an interface between the coupling plate 26 and the camera 12. Additional types of sensors 29 may be deployed.

Referring to FIG. 1, the robotic arm 24 (and/or coupling plate 26) may be controlled via the controller C and/or an integrated processor, such as a robotic arm controller 42. The robotic arm 24 may be selectively operable to extend a viewing range of the camera 12 along an X-axis, a Y-axis and a Z-axis. The robotic arm controller 42 may include a processor, a server, a microcontroller, a workstation, etc. configured to convert one or more messages or instructions from the controller C into messages and/or signals that cause any one of the joints to rotate. The robotic arm controller 42 is also configured to receive and convert sensor information, such as joint position and/or speed from the robotic arm 24 and/or the coupling plate 26 into one or more messages for the controller C. U.S. application Ser. No. 16/398,014 (filed on Apr. 29, 2019), the contents of which is hereby incorporated by reference in its entirety, describes a stereoscopic visualization camera with an integrated robotics platform.

The head unit 18 may be connected to a cart 34 having at least one display medium (which may be a monitor, terminal or other form of two-dimensional visualization), such as first and second displays 36 and 38 shown in FIG. 1. Referring to FIG. 1, the controller C may be configured to process signals for broadcasting on the first and second displays 36 and 38. The housing assembly 20 may be self-contained and movable between various locations. The image stream from the camera 12 may be sent to the controller C and/or a camera processor (not shown), which may be configured to prepare the image stream for viewing. For example, the controller C may combine or interleave first and second video signals from the camera 12 to create a stereoscopic signal. The controller C may be configured to store video and/or stereoscopic video signals into a video file and stored to memory M. The first and second displays 36 and 38 may incorporate a stereoscopic display system, with a two-dimensional display having separate images for the left and right eye respectively. To view the stereoscopic display, a user may wear special glasses that work in conjunction with the first and second displays 36, 38 to show the left view to the user's left eye and the right view to the user's right eye.

Referring to FIG. 1, the first display 36 may be connected to the cart 34 via a flexible mechanical arm 40 with one or more joints to enable flexible positioning. The flexible mechanical arm 40 may be configured to be sufficiently long to extend over a patient during surgery to provide relatively close viewing for a surgeon. The first and second displays 36, 38 may include any type of display, such as a high-definition television, an ultra-high-definition television, smart-eyewear, projectors, one or more computer screens, laptop computers, tablet computers, and/or smartphones and may include a touchscreen.

The camera 12 is configured to acquire images of the target site 16, which may be presented in different forms, including but not limited to, captured still images, real-time images and/or digital video signals. "Real-time" as used herein generally refers to the updating of information at the same rate as data is received. More specifically, "real-time" means that the image data is acquired, processed, and transmitted at a high enough data rate and a low enough delay that when the data is displayed, objects move smoothly without user-noticeable judder or latency. Typically, this occurs when new images are acquired, processed, and transmitted at a rate of at least about 30 frames per second (fps) and displayed at about 60 fps and when the combined processing of the video signal has no more than about $1/30^{th}$ second of delay.

Figure 3:
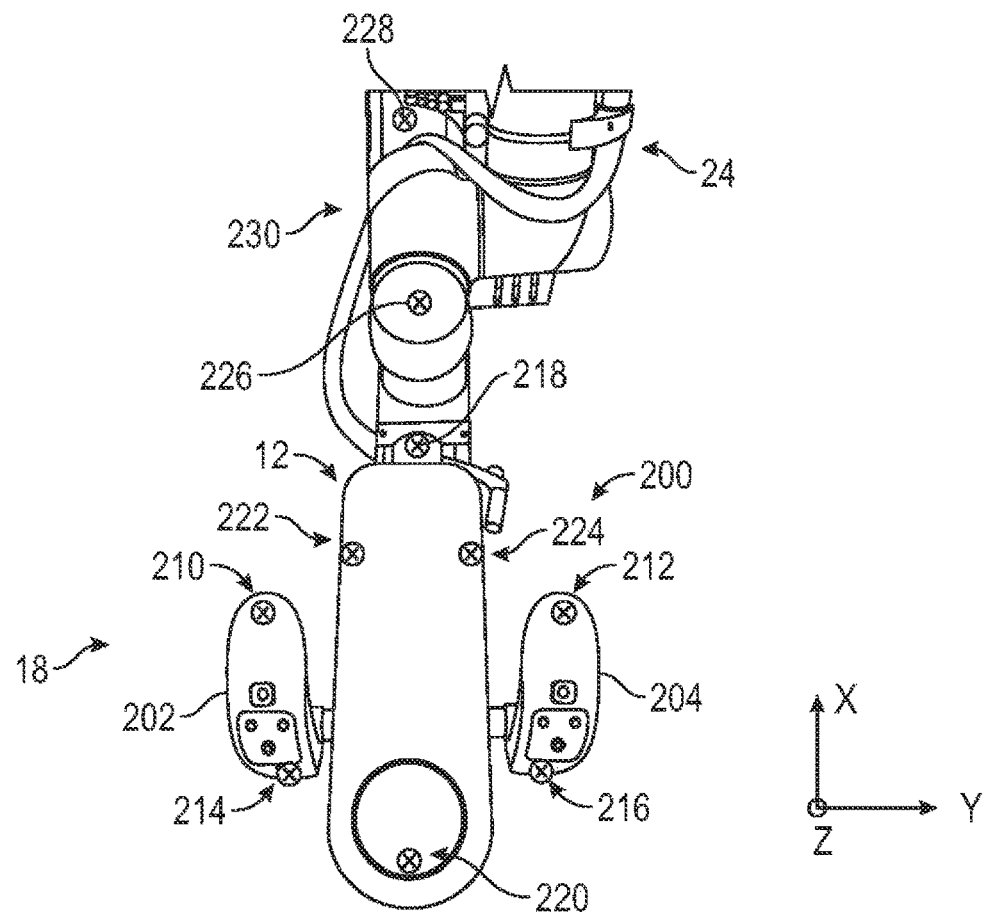
FIG. 3 is a schematic fragmentary top view of the robotic imaging system of FIG. 1, illustrating one or more checkpoints.

The controller C is adapted to calculate the respective correction force for one or more checkpoints 200 located on the head unit 18, the robotic arm 24, and other places, as shown in FIG. 3. The checkpoints 200 each have a respective position and a respective speed, both along a first direction (e.g., x-direction in FIG. 3). The position and velocity of each of the checkpoints 200 can be calculated with respect to a fixed coordinate frame (for example, either a camera frame or a robot base frame). The fixed coordinate frame may be chosen or varied based on the application at hand. Referring to FIG. 3, The checkpoints 200 may include multiple points on the input device 22, the head unit 18, the coupling plate 26 and the robotic arm 24. Referring to FIG. 3, the input device 22 may include a first handle 202 and a second handle 204. In some embodiments, the input device 22 includes multiple checkpoints such as a first handle top point 210, a first handle bottom point 214, a second handle top point 212 and a second handle bottom point 216. Referring to FIG. 3, the checkpoints 200 may include respective points on the head unit 18, such as a camera proximal point 218, a camera distal point 220, a first side camera mid-point 222, and a second side camera mid-point 224. The set of checkpoints 200 may further include a tool center point 226 and a joint extrusion point 228 in joint 230 of the robotic arm 24.

Figure 4:
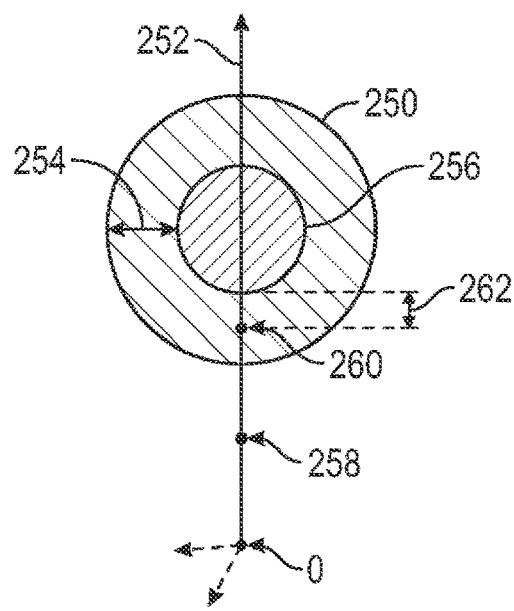
FIG. 4 is a schematic fragmentary diagram showing a buffering distance from a keep-out zone for a checkpoint.

The collision avoidance mode 14 of FIG. 1 is activated when the camera 12 and/or the robotic arm 24 enter a predefined region, such as predefined buffer zone 250 shown in FIG. 4. The predefined buffer zone 250 is shown with respect to a reference axis 252 extending from an origin O. The predefined buffer zone 250 is within a delta value 254 of at least one "keep-out" region, such as keep-out zone 256. The application of the correction force pushes the camera 12 and/or robotic arm 24 away from the keep-out zone 256, which would otherwise cause a collision. As an example, the first reference point 258 of FIG. 4 is not in the predefined buffer zone 250, thus no correction force would be applied. However, the second reference point 260 is within the predefined buffer zone 250 (within a buffering distance 262) and a correction force would be applied.

The correction force may be calculated using feedback control with a closed-loop control module. The closed-loop control module may be a proportional-integral controller, a proportional-derivative controller or a proportional-integral-derivative controller. For example, the respective correction force for the checkpoints 200 using a proportional-derivative controller as: $F=[K_p(b-x)+K_d(0-\dot{x})$, if $x>b$.] Here F denotes the respective correction force, b denotes the respective buffering distance 262 to the keep-out zone 256, x denotes the respective position, and $\dot{x}$ denotes the respective speed of each of the checkpoints 200. Here, Kp and Kd are the proportional and derivative constants, respectively, from the PD controller, with the process variable being a difference between the buffering distance (b) and the current position (x). The constants Kp and Kd may be tuned via a calibration process with known changes in position and speed. In this embodiment, the controller C can also inject a small amount of damping to the control system dynamics, further improving the smoothness and eliminating oscillations caused by user input.

Figure 2:
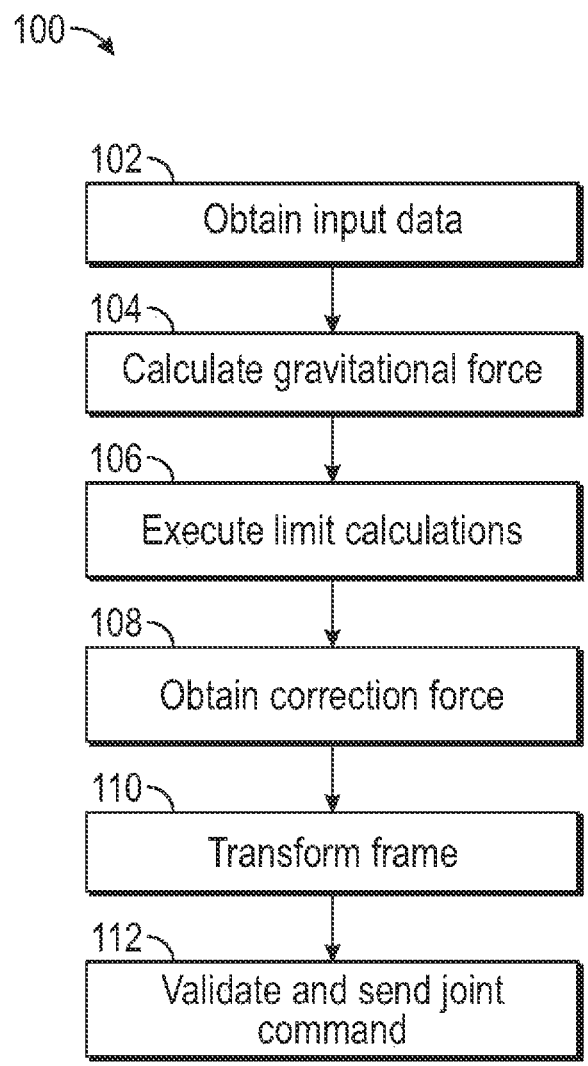
FIG. 2 is a flowchart of an example method for operating the collision avoidance mode.

Referring now to FIG. 2, a flowchart is shown of an example method 100 for operating the collision avoidance mode 14 of FIG. 1. Method 100 may be embodied as computer-readable code or instructions stored on and partially executable by the controller C of FIG. 1. Method 100 need not be applied in the specific order recited herein and may be dynamically executed. Furthermore, it is to be understood that some steps may be eliminated. Method 100 may be executed periodically or at predefined time intervals.

Method 100 begins with block 102 of FIG. 2, where the controller C is programmed to receive input data, such as joint position data of the robotic arm 24 and sensor data from the force-based sensor 28 related to force and/or torque imparted by a user on the camera 12. The sensor data includes an input force vector representing the forces imparted by the user and/or an input torque vector representing the torque imparted by the user. Also, per block 102, the method 100 may include filtering the sensor data, e.g., with a first low-pass filter, a second low pass filter, and/or a notch filter that targets cart vibrations. In some embodiments, no filtering is applied.

Proceeding to block 104 of FIG. 2, the controller C is programmed to calculate gravitational force and apply gravity compensation by removing the effects of Earth's gravity from the sensor data. Gravity calculation software available to those skilled in the art may be employed.

Advancing to block 106 in FIG. 2, the controller C is programmed to execute a plurality of spatial limit or boundary calculations. The spatial limits may be defined in joint space, Cartesian space or another suitable coordinate frame. An example execution of a cart limit calculation 300, a boundary plane limit calculation 400, and a joint limit calculation 500, are described below with respect to FIGS. 5-8. It is understood that other limit calculations may be employed.

Cart Limit Calculation.

Figure 5:
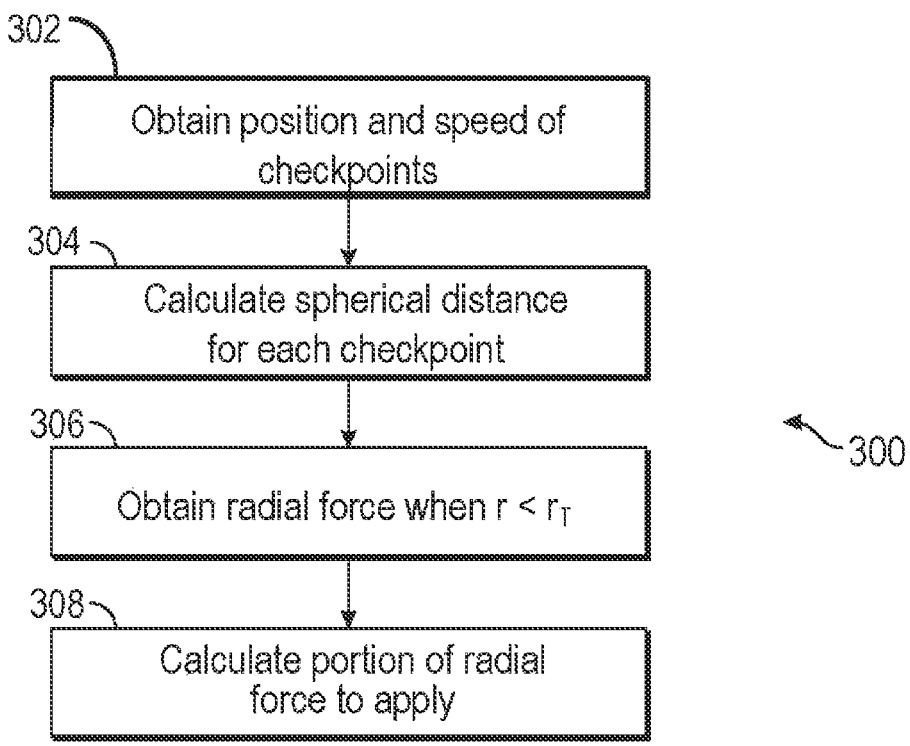
FIG. 5 is a flowchart of a portion of the method of FIG. 2, illustrating an example cart limit calculation.
Figure 6:
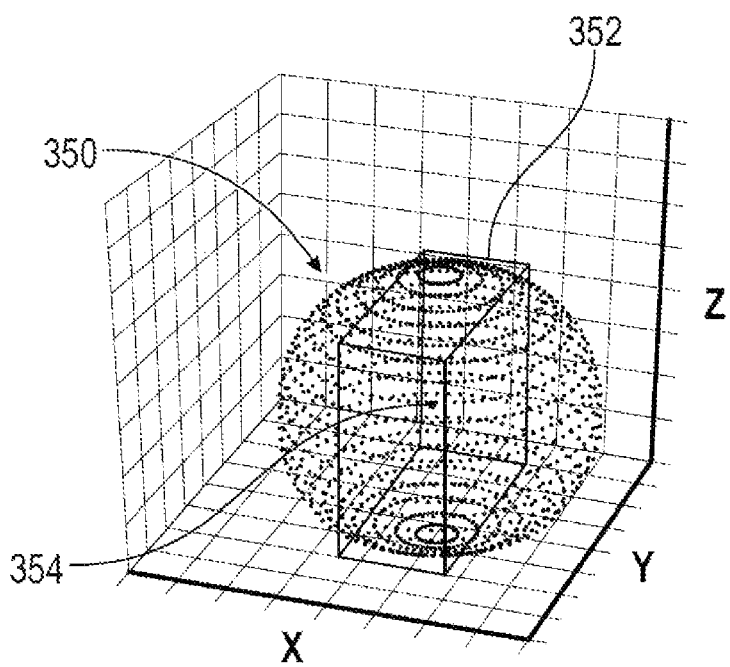
FIG. 6 is a schematic graph illustrating a model of a cart surface employable in the cart limit calculation of FIG. 5.

Referring to FIG. 5, a flowchart of an example execution of the cart limit calculation 300 is shown. Per block 302 of FIG. 5, the controller C is programmed to obtain the respective position (and speed) of the checkpoints 200, e.g., relative to the origin O in FIG. 4. Proceeding to block 304 of FIG. 5, the controller C is programmed to calculate the respective spherical distance and respective speed for the checkpoints 200 from the surface of the cart 34. The surface of the cart 34 may be modelled as a sphere. FIG. 6 is a schematic graph illustrating modelling of the surface of the cart, with a bounding sphere 350 and a bounding rectangle 352 used to bound the cart geometry. The respective spherical distance (r) is obtained as: $r = \sqrt{(w_0-s_0)^2+(w_1-s_1)^2+(w_2-s_2)^2}$, with $(w_0, w_1, w_2)$ denoting the respective coordinates of the checkpoints 200 and $(s_0, s_1, s_2)$ denoting respective coordinates of the center 354 of the bounding sphere 350. The respective speed ($\dot{r}$) may be obtained based on the respective coordinates of the center of the sphere 350 and a time derivative of the respective coordinates of the at least one checkpoint. The respective speed ($\dot{r}$) is obtained as shown below, with $(\dot{w}_0, \dot{w}_1, \dot{w}_2)$ denoting a time derivative of the respective coordinates of the checkpoints 200.

$$\dot{r} = \frac{\dot{w}_0(w_0 - s_0) + \dot{w}_1(w_1 - s_1) + \dot{w}_2(w_2 - s_2)}{r}$$

Proceeding to block 306 of FIG. 5, the controller C is programmed to obtain a radial force when the respective spherical distance is below a predefined threshold, when $r<r_T$. The radial force ($F_R$) may be obtained using a proportional-derivative controller based in part on the respective spherical distance (r), the respective speed ($\dot{r}$), a buffering distance to the at least one keep-out zone, and a plurality of tunable constants. For example, the radial force is obtained as: $[F_R=[K_p(b-r)+K_d(0-\dot{r})]$, where r is the respective spherical distance, $\dot{r}$ is the respective speed, b is the buffering distance from the checkpoint 200 to the at least one keep-out zone 256, and $K_p$, $K_d$ are the plurality of tunable constants.

Advancing to block 308 of FIG. 5, the controller C is programmed to calculate the force contribution to the correction force. The force contribution may be obtained as the radial force ($F_R$) multiplied by a fraction (f). In some embodiments, the fraction $$\left(f = \frac{(w_i - s_i)}{r}\right).$$

Stated differently, the force contribution is set as a new vector having the magnitude of the radial force ($F_R$) (calculated in block 306) and having a direction pointing radially outward from the center of the sphere to the checkpoint.

Boundary Plane Limit Calculation.

Figure 7:
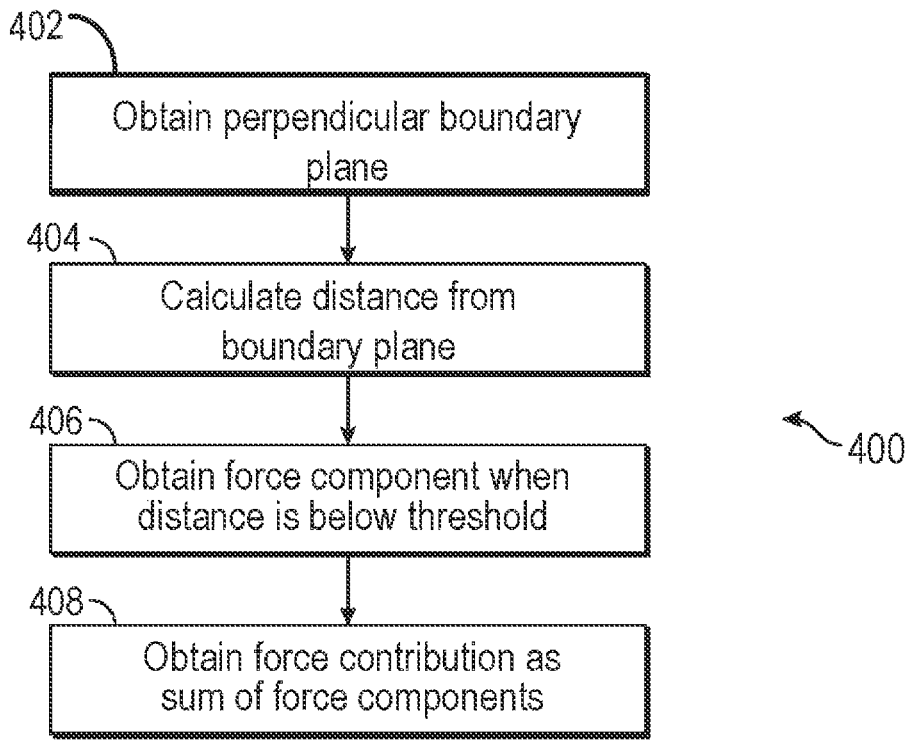
FIG. 7 is a flowchart of a portion of the method of FIG. 2, illustrating an example boundary plane limit calculation.

Referring to FIG. 7, a flowchart of an example execution of the boundary plane limit calculation 400 is shown. Per block 402 of FIG. 7, the controller C is programmed to obtain at least one boundary plane 52 (see FIG. 1) perpendicular relative to a first direction (e.g., the Z-axis in FIG. 1). The boundary plane 52 may be in proximity to a patient, for example within a clearance distance. Proceeding to block 404 of FIG. 7, the controller C is programmed to obtain a respective distance (z) and a respective speed ($\dot{z}$) along the first direction (e.g., the z direction in FIG. 1) of the checkpoints 200 from the boundary plane 52.

Advancing to block 406 of FIG. 7, the controller C is programmed to calculate the respective force components when the respective distance (z) is below a predefined threshold (b). Each force component ($F_i$) is obtained as: $[F_i=[K_p(b-z)+K_d(0-\dot{z})]$, where z is the respective distance (from the origin of the XYZ axis in FIG. 1) along the first direction, $\dot{z}$ is the respective speed along the first direction, b is the respective buffering distance to the keep-out zone 256, and $K_p$, $K_d$ are the plurality of tunable constants. Per block 408 of FIG. 7, the force contribution is obtained as a sum of the respective force components $\Sigma$ Fi).

Joint Limit Calculation.

Figure 8:
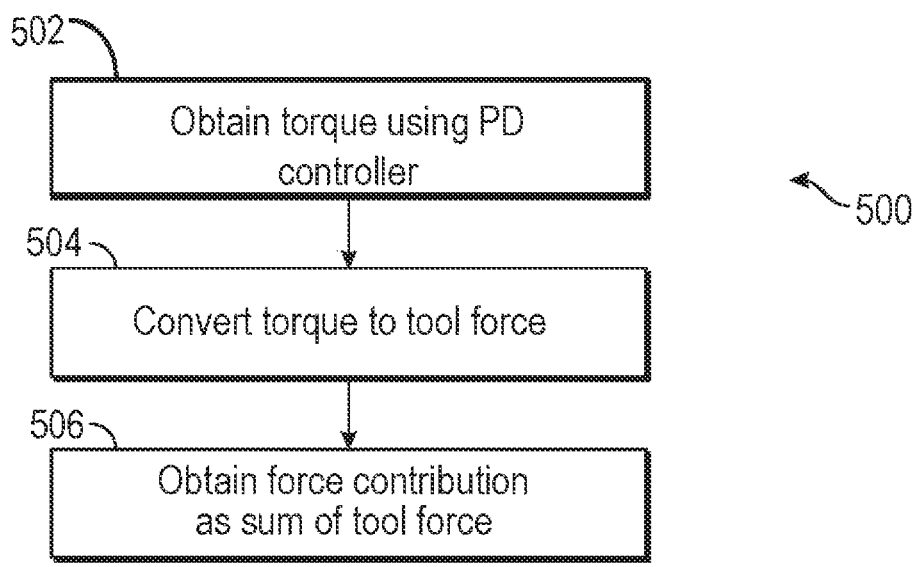
FIG. 8 is a flowchart of a portion of the method of FIG. 2, illustrating an example joint limit calculation.

Referring to FIG. 8, a flowchart of an example execution of the joint limit calculation 500 is shown. Per block 502 of FIG. 8, the controller C is programmed to determine a respective torque for each of the joints (such as first joint 30 and second joint 32 shown in FIG. 1) in the robotic arm 24. The respective torque ($\tau_i$) is obtained as: $[\tau_i=[K_p(b-y)+K_d(0-\dot{y})]$, where y is the respective distance (from the origin of the XYZ axis in FIG. 1) of the joint, $\dot{y}$ is the respective speed, b is the respective buffering distance to a keep-out zone, and $K_p$, $K_d$ are tunable constants of a proportional-derivative controller.

Proceeding to block 504 of FIG. 8, the controller C is programmed to convert the respective torque ($\tau$) to a respective tool force (F') for each joint, using a transpose of a Jacobian matrix (e.g., using $\tau=J(q)^T F'$). After the tool force is calculated using the transpose of the Jacobian and the joint torque is obtained, a tuning constant is obtained for each joint. The tuning constant can be set as either 0 or 1 and is employed to selectively enable or disable individual axes. Advancing to block 506 of FIG. 8, the controller C may obtain the force contribution as a sum of the respective tool force ($\Sigma$ F') for each of the joints (modulated by the tuning constant).

Referring now to FIG. 2, method 100 proceeds to block 108, where the controller C is programmed to obtain the correction force as a sum of respective force contributions from the plurality of limit calculations (obtained in block 106). The correction force is applied to the movement sequence, to modify the movement sequence, when the camera 12 and/or the robotic arm 24 enter the predefined buffer zone 250 (see FIG. 4). The movement sequence is obtained using kinematics, for example, inverse kinematics and/or Jacobian kinematics (e.g., an inversion of a Jacobian matrix). The controller C determines a movement sequence that specifies how certain joints of the robotic arm and/or coupling plate 26 are to move in a coordinated manner and specifies, for example, joint rotation speed, joint rotational direction, and/or joint rotational duration. The movement sequence may also specify a sequence in which joints of the robotic arm 24 and/or the coupling plate 26 are to be rotated. Any of the joints of the robotic arm 24 and/or coupling plate 26 may rotate individually or have overlapping movement depending on the movement sequence. The Jacobian kinematic equations define how certain joints of the robotic arm 24 and/or the coupling plate 26 are to be moved based on the scaled translational/rotational vector(s). The Jacobian kinematics provide for speed control while inverse kinematics provide for positional control. Other robotic arm control routines may be employed.

Advancing to block 110 in FIG. 2, the method 100 includes transforming coordinates from the sensor (force/torque) frame to a robot base frame, which is the coordinate axis on the cart 34 where the base of the robotic arm 24 is mounted. The controller C is programmed to use the joint position data in conjunction with the compensated, filtered force/torque output data to perform this coordinate transformation. The transformation may include one or more pre-defined equations or relations based on the position and orientation of the force-based sensor 28. The transformation may be based on parameters obtained via calibration. In one embodiment where the assisted drive function 50 operates in the camera frame (on the input side), the joint, boundary, and cart limits may be analytically computed in the robot base frame and converted back to the camera frame before the signal is sent back to the assisted drive function 50.

Proceeding to block 112 of FIG. 2, the controller C is programmed to validate a command to ensure that a command (or signal indicative of a command) is within operating parameters (e.g., duration, rotational speed, etc.) of a joint motor. The controller C and/or the robotic arm controller 42 may also validate a command by comparing the command to current thresholds to ensure the robotic arm 24 will not draw excess current during any phase of the movement sequence. Also, per block 112 of FIG. 2, the controller C is programmed to transmit the commands via one or more signals to the appropriate joint motor of the robotic arm 24 and/or the coupling plate 26 according to the movement sequence. The transmitted commands cause motors at the respective joints to move the robotic arm 24 and/or the coupling plate 26, thereby causing the camera 12 to move while avoiding collisions.

The controller C of FIG. 1 may include, or otherwise have access to, information downloaded from remote sources and/or executable programs. Referring to FIG. 1, the controller C may be configured to communicate with a remote server 60 and/or a cloud unit 62, via a network 64. The remote server 60 may be a private or public source of information maintained by an organization, such as for example, a research institute, a company, a university and/or a hospital. The cloud unit 62 may include one or more servers hosted on the Internet to store, manage, and process data.

The network 64 may be a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data. The network 64 may be a Wireless Local Area Network (LAN) which links multiple devices using a wireless distribution method, a Wireless Metropolitan Area Network (MAN) which connects several wireless LANs or a Wireless Wide Area Network (WAN) which covers large areas such as neighboring towns and cities. Other types of connections may be employed.

The controller C of FIG. 1 may be an integral portion of, or a separate module operatively connected to the robotic imaging system 10. The controller C includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic media, a CD-ROM, DVD, other optical media, punch cards, paper tape, other physical media with patterns of holes, a RAM, a PROM, an EPROM, a FLASH-EEPROM, other memory chips or cartridges, or other media from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The flowcharts presented herein illustrate an architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by specific purpose hardware-based devices that perform the specified functions or acts, or combinations of specific purpose hardware and computer instructions. These computer program instructions may also be stored in a computer-readable medium that can direct a controller or other programmable data processing apparatus to function in a particular manner, such that the instructions stored in the computer-readable medium produce an article of manufacture including instructions to implement the function/act specified in the flowchart and/or block diagram blocks.

The numerical values of parameters (e.g., of quantities or conditions) in this specification, including the appended claims, are to be understood as being modified in each respective instance by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of each value and further divided ranges within the entire range. Each value within a range and the endpoints of a range are hereby disclosed as separate embodiments.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A robotic imaging system comprising:
   a camera configured to record one or more images of a target site;
   a robotic arm operatively connected to the camera, the robotic arm being adapted to selectively move the camera in a movement sequence, the robotic arm including one or more joints;
   a force-based sensor configured to detect and transmit sensor data related to at least one of force and/or torque imparted by a user for moving the camera;
   a controller configured to receive the sensor data, the controller having a processor and tangible, non-transitory memory on which instructions are recorded;
   wherein the controller is adapted to selectively execute a collision avoidance mode, including applying a respective correction force to modify the movement sequence when at least one of the camera and the robotic arm enter a predefined buffer zone, the predefined buffer zone being within a delta value of at least one keep-out zone; and
   wherein the controller is adapted to apply the respective correction force to push at least one of the camera and the robotic arm away from the at least one keep-out zone.

2. The robotic imaging system of claim 1, wherein:
   the camera is a stereoscopic camera configured to record a left image and a right image for producing at least one stereoscopic image of the target site.

3. The robotic imaging system of claim 1, wherein:
   the force-based sensor includes a six-degrees-of-freedom haptic force-sensing device.

4. The robotic imaging system of claim 1, wherein:
   the controller is adapted to calculate the respective correction force using a closed-loop control module, including at least one of a proportional-integral controller, a proportional-derivative controller and a proportional-integral-derivative controller.

5. The robotic imaging system of claim 1, wherein the controller is adapted to calculate the respective correction force for one or more checkpoints each having a respective position and respective speed along a first direction.

6. The robotic imaging system of claim 5, further comprising:
   a head unit for housing the camera;
   a coupling plate mechanically coupling the head unit to the robotic arm, the head unit being operatively connected to a cart; and
   wherein the one or more checkpoints are located on at least one of the head unit, the coupling plate and the robotic arm.

7. The robotic imaging system of claim 5, wherein:
   the controller is adapted to calculate the respective correction force using a proportional-derivative controller as: $F=[K_p(b-x)+K_d(0-\dot{x})]$, with F denoting the respective correction force, b denoting a respective buffering distance to the at least one keep-out zone, x and $\dot{x}$ denoting the respective position and respective speed of the one or more checkpoints, and $K_p$ and $K_d$ denoting respective tunable gain factors of the proportional-derivative controller.

8. The robotic imaging system of claim 1, wherein the controller is adapted to execute a joint limit calculation, the respective correction force including a force contribution from the joint limit calculation.

9. The robotic imaging system of claim 8, wherein executing the joint limit calculation includes:
   determining a respective torque for the at least one joint, via a closed-loop module; and
   converting the respective torque to a respective tool force using a transpose of a Jacobian matrix, the force contribution being based on a sum of the respective tool force for each of the one or more joints.

10. The robotic imaging system of claim 1, further comprising:
    a cart operatively connected to the robotic arm;
    wherein the respective correction force includes a force contribution from a cart limit calculation;
    wherein the controller is adapted to execute the cart limit calculation, including:
        calculating a respective spherical distance and a respective speed of one or more checkpoints from a surface of the cart;
        obtaining a radial force when the respective spherical distance is below a predefined threshold; and
    wherein the force contribution is obtained as the radial force multiplied by a fraction.

11. The robotic imaging system of claim 10, wherein:
    the surface of the cart is modelled as a sphere and the respective spherical distance (r) is obtained as:

$$r = \sqrt{(w_0 - s_0)^2 + (w_1 - s_1)^2 + (w_2 - s_2)^2},$$

with $(w_0, w_1, w_2)$ denoting respective coordinates of the one or more checkpoints and $(s_0, s_1, s_2)$ denoting the respective coordinates of a center of the sphere.

12. The robotic imaging system of claim 11, wherein the respective speed ($\dot{r}$) is obtained based in part on the respective coordinates of the center of the sphere and a time derivative of the respective coordinates of the one or more checkpoints.

13. The robotic imaging system of claim 12, wherein the respective speed ($\dot{r}$) is obtained as $$\dot{r} = \frac{\dot{w}_0(w_0 - s_0) + \dot{w}_1(w_1 - s_1) + \dot{w}_2(w_2 - s_2)}{r},$$

with $(\dot{w}_0, \dot{w}_1, \dot{w}_2)$ denoting the time derivative of the respective coordinates of the one or more checkpoints.

14. The robotic imaging system of claim 11, wherein the controller is adapted to calculate the radial force based in part on a respective buffering distance to the at least one keep-out zone, the respective spherical distance and the respective speed.

15. The robotic imaging system of claim 14, wherein the radial force is obtained as: [F_R=]K_p(b−r)+K_d(0−$\dot{r}$)], where r is the respective spherical distance, $\dot{r}$ is the respective speed, b is the respective buffering distance to the at least one keep-out zone, and $K_p$, $K_d$ are a plurality of tunable constants of a proportional-derivative controller.

16. The robotic imaging system of claim 1, wherein:
    the respective correction force includes a force contribution from a boundary plane limit calculation, the controller being adapted to execute the boundary plane limit calculation, including:
        obtaining at least one boundary plane perpendicular relative to a first direction;
        calculating a respective distance and a respective speed of one or more checkpoints from the at least one boundary plane along the first direction;
        obtaining respective force components when the respective distance is below a predefined threshold; and
        obtaining the force contribution as a sum of each of the respective force components.

17. The robotic imaging system of claim 16, wherein the at least one boundary plane is in proximity to a patient.

18. The robotic imaging system of claim 16, wherein the controller is adapted to calculate the respective force components based in part on a respective buffering distance to at least one keep-out zone, the respective distance and the respective speed from the at least one boundary plane.

19. The robotic imaging system of claim 18, wherein the respective force components ($F_i$) are obtained as: [F_i=/ [K_p(b−z)+K_d(0−$\dot{z}$)], where z is the respective distance from the at least one boundary plane, $\dot{z}$ is the respective speed, b is the respective buffering distance to the at least one keep-out zone, and $K_p$, $K_d$ are a plurality of tunable constants of a proportional-derivative controller.

20. A robotic imaging system comprising:
    a camera configured to record one or more images of a target site;
    a robotic arm operatively connected to the camera, the robotic arm being adapted to selectively move the camera in a movement sequence, the robotic arm including one or more joints;
    a force-based sensor configured to detect and transmit sensor data related to at least one of force and/or torque imparted by a user for moving the camera;
    a controller configured to receive the sensor data, the controller having a processor and tangible, non-transitory memory on which instructions are recorded;
    wherein the controller is adapted to selectively execute a collision avoidance mode, including applying a respective correction force to modify the movement sequence when at least one of the camera and the robotic arm enter a predefined buffer zone, the predefined buffer zone being within a delta value of at least one keep-out zone;
    wherein the controller is adapted to apply the respective correction force to push at least one of the camera and the robotic arm away from the at least one keep-out zone; and
    wherein the respective correction force includes force contributions from a boundary plane limit calculation, a cart limit calculation and a joint limit calculation.

* * * * *